US005301878A

United States Patent [19]

Sinclair et al.

[11] Patent Number: 5,301,878
[45] Date of Patent: Apr. 12, 1994

[54] DEVICE FOR PRODUCING A PARTICULATE DISPERSION

[75] Inventors: Colin S. Sinclair, Manchester; Alan Tallentire, Cheshire, both of United Kingdom

[73] Assignee: The Victoria University of Manchester, Manchester, England

[21] Appl. No.: 836,344

[22] PCT Filed: Aug. 2, 1990

[86] PCT No.: PCT/GB90/01198

§ 371 Date: Apr. 1, 1992

§ 102(e) Date: Apr. 1, 1992

[87] PCT Pub. No.: WO91/03270

PCT Pub. Date: Mar. 21, 1991

[30] Foreign Application Priority Data

Sep. 1, 1989 [GB] United Kingdom ................ 8919767

[51] Int. Cl.$^5$ .............................................. A61M 11/00

[52] U.S. Cl. .................................... 239/338; 239/369; 239/424.5

[58] Field of Search ............... 239/338, 370, 340, 369, 239/371, 424.5, 431, 434; 128/200.14, 200.18, 200.21

[56] References Cited

U.S. PATENT DOCUMENTS

| | | | |
|---|---|---|---|
| 2,789,867 | 4/1957 | Bloom et al. | 239/431 |
| 4,588,129 | 5/1986 | Shanks | 239/338 |
| 4,674,491 | 6/1987 | Brugger et al. | 239/338 |

FOREIGN PATENT DOCUMENTS

| | | |
|---|---|---|
| 248894 | 7/1912 | Fed. Rep. of Germany . |
| 513052 | 11/1930 | Fed. Rep. of Germany . |
| 2019743 | 11/1979 | United Kingdom . |

*Primary Examiner*—Andres Kashnikow
*Assistant Examiner*—Lesley D. Morris
*Attorney, Agent, or Firm*—Nies, Kurz, Bergert & Tamburro

[57] ABSTRACT

A nebulizer for liquids, particulate materials or liquids/-solids suspensions, comprising, within a vessel (10) containing a reservoir (11), an upright duct (13) with a plurality of circumferentially spaced outlet apertures (20), enclosing a coaxial air line (14) feeding a plurality of jets (16) duly aligned with outlet apertures (20) in the upright duct (13) so that an annular column of material is drawn from reservoir (11) to be dispersed by entrainment in the air streams from the jets (16). Larger droplets may return to the reservoir (11) while the smaller fraction issues from the vessel through an outlet (12). The relatively large outlet apertures (20) and the large cross-sectional area of the column of the material prevent blockage at the nebulizer head.

9 Claims, 2 Drawing Sheets

DEVICE FOR PRODUCING A PARTICULATE DISPERSION

BACKGROUND AND SUMMARY OF THE INVENTION

This invention concerns a device for the production of a substantially uniform dispersion of droplets or particles from a fluid material such as a liquid or solids/liquids suspensions, or particulate free-flowing solids. Such aerosols or dispersions are widely used in the biological and medical research fields and in inhalation therapy, and are generated by the aerosolization of the liquid or other particulate substance by an air stream. The efficiency of the process is dependent upon the flow of the material through an orifice or jet.

In practice, when the material to disperse is or contains solid particles, the orifice or jet tends to block, thus restricting the use of such devices primarily to particle-free liquids.

It is an object of the present invention to provide a device which may be used to disperse materials containing solids in suspension or even dry particulate materials.

According to the present invention there is provided a device for producing a particulate dispersion, comprising at least one duct in which may be established and maintained a supply of a fluid material to be dispersed, a plurality of outlet apertures communicating with the or each duct and directed generally normal to the longitudinal axis of the or each duct, and a plurality of pressurised gas jets aligned or movable into alignment with the outlet apertures to force material through the latter from the or each duct thus to form a dispersion; characterised in that the cross-sectional area of each outlet aperture is not greater than the cross-sectional area of the duct communicating therewith.

BRIEF DESCRIPTION OF THE DRAWINGS

Embodiments of the invention will now be described, by way of example only, with reference to the accompanying drawings in which.

DESCRIPTION OF THE PREFERRED EMBODIMENTS

Figure 1:
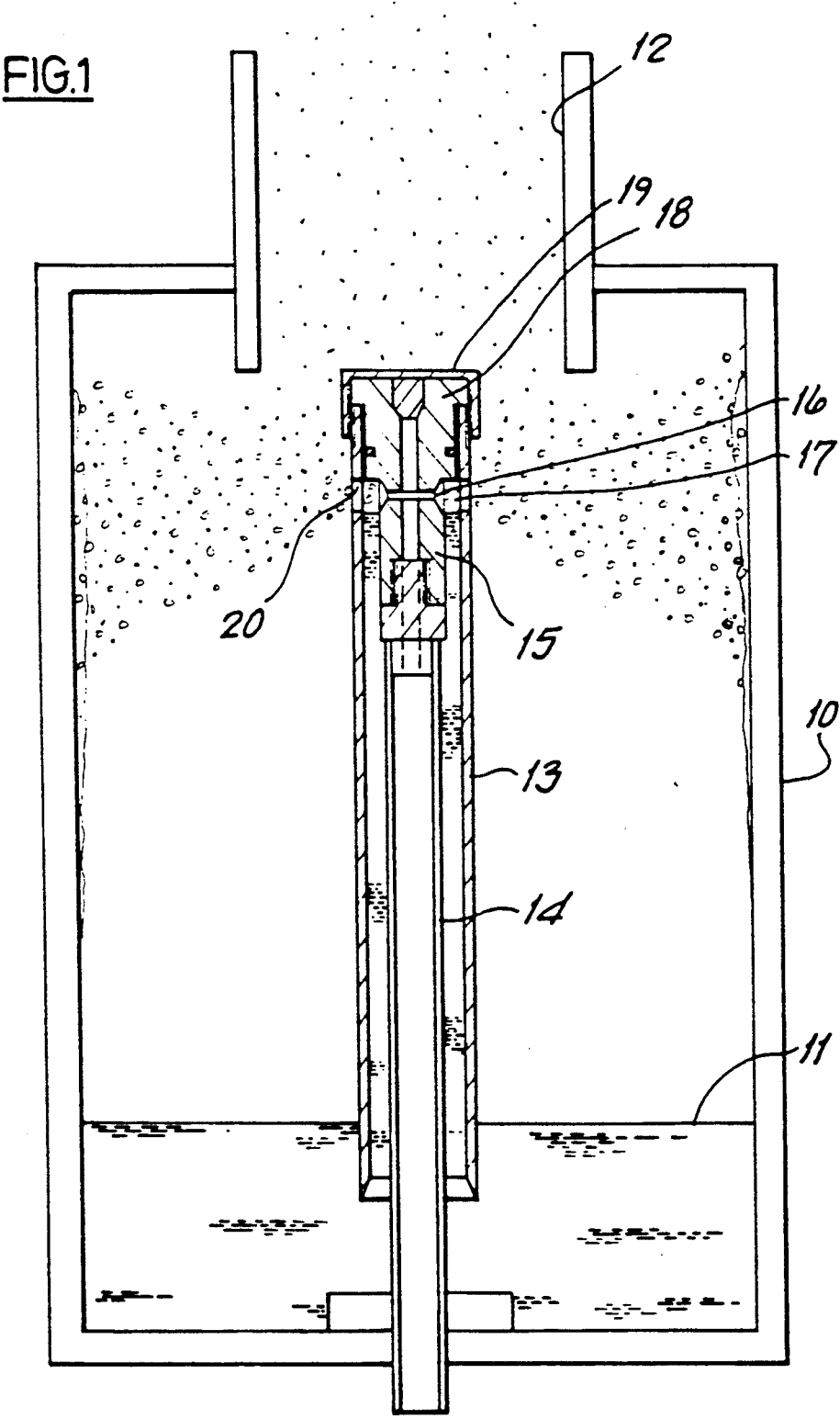
FIG. 1 illustrates, partly in vertical cross-section a first form of device made in accordance with the invention.

Referring now to FIG. 1, a device for producing a particulate dispersion comprises a vessel 10 for containing a reservoir 11 of liquid or a liquid/solids suspension. The vessel includes a wide outlet duct 12 which in this example is directed upwardly at the top of the vessel. A nebulizer assembly comprises an upright tubular duct 13 fixed centrally within the vessel 10 and aligned with the outlet 12, and having its lower open end submerged within the reservoir 11. Concentrically within the duct 13 is an air line 14 connected externally of the vessel 10 to a supply of pressurized air. At the top of the air line 14 is a body 15 defining a plurality of air jets 16 which communicate with the air line 14 each having a diverging mouth 17 opening into the column of liquid established within the duct 13. The assembly of duct 13 and body 15 is closed at its upper end by a sealed plug 18 and cap 19. These latter parts are removable for cleaning.

In the wall at the top of duct 13 a number of outlet apertures 20 are aligned with the air jets 16.

Some six to twelve aligned pairs of air jets 16 and apertures 20 may be provided at spaced positions around the circumference of duct 13.

In operation therefore the pressurized air issuing from jets 16 impinges upon the liquid at the top of the column within duct 13 and forms a dispersion of droplets of liquid as an aerosol which passes outwardly through apertures 20. The sizes of droplets of liquid within the aerosol vary and in the case of water may be between 0.5 $\mu$m and 500 $\mu$m. Thus it is possible to disperse a suspension of solids particles within a liquid provided that the particle size is less than the diameter of the apertures 20.

The dimensions of the parts of the assembly illustrated in FIG. 1 in this example, are such that the combined cross-sectional area of the apertures 20 is not greater than and preferably less than the cross-sectional area of the annular column of liquid in duct 13, but is greater than the combined cross-sectional area of the air jets 16. Thus, the liquid /solids are not required to flow through a small constriction and there is no tendency for the apertures 20 to become blocked.

It will be seen that larger droplets within the size range produced impinge upon the walls of vessel 10 and may thus flow back into the reservoir 11, whilst the smaller droplets form a uniform dispersion which issues from the vessel via outlet 12.

The droplets in the product aerosol issuing from outlet 12 are typically in the range of 0.5 $\mu$m to 20 $\mu$m. The maximum droplet size is determined by the geometry of the apparatus and is inversely related to the level of impaction forces generated by the input pressure applied to the air jets.

Figure 2:
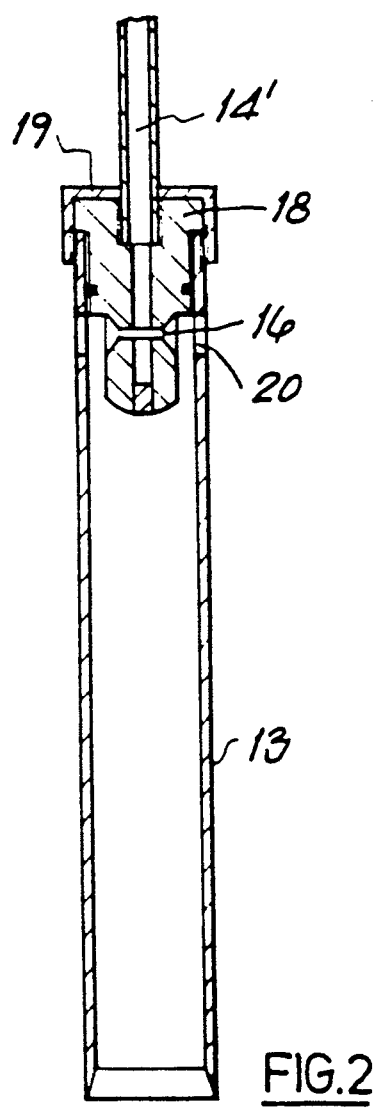
FIG. 2 illustrates a modified form of part of the device illustrated in FIG. 1.

Referring now to FIG. 2, the nebulizer assembly within vessel 10 is modified in that the air line illustrated at 14' enters the assembly from the top, leaving the entire duct 13 free to transport a liquid column of larger cross-sectional area from the reservoir.

Figure 3:
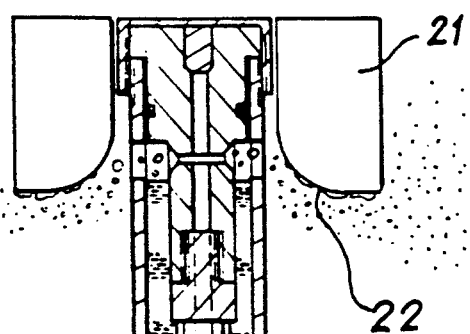
FIG. 3 illustrates in vertical cross-section a further form of device made in accordance with the invention.
Figure 3:
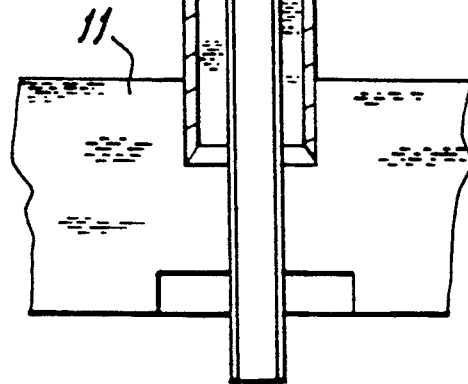

Referring now to FIG. 3, in an embodiment generally similar to that shown in FIG. 1, there may be included a baffle 21 which surrounds the top of duct 13 and presents, adjacent each outlet aperture 20 a curvilinear or other outwardly diverging surface 22 upon which larger droplets within the dispersion may impinge.

The high velocity of air flow across the surfaces 22 results in secondary production of small droplets by a re-entrainment of the impacted liquid so that the overall droplet size falls within a similar range to that produced by the apparatus illustrated in FIG. 1, but here aerosol concentration is significantly greater since less of the liquid is returned to the reservoir. Again, the maximum droplet size and the extent of secondary aerosol production are determined by the geometry of the apparatus and are inversely and directly related respectively to the input pressure.

It should be noted that in all embodiments of the invention, for a volatile liquid, aerosolized droplets will evaporate with time to a new size. The extent of evaporation is dependent upon the vapour pressure of the liquid in air. If solutes and/or insoluble particles are present in the liquid, complete evaporation can leave almost dry particles of solute and/or insoluble particles dispersed in the air.

Typically, the air jets 16 may be six in number equidistant around the body 15, and between 0.7 and 1.3 mm in diameter with the outlet apertures 20 between 3 and 6 mm in diameter. The cross-sectional area of the duct 13 would accordingly be between 140 sq mm and 420 sq mm. In general, increasing the size of the outlet apertures requires an increased air flow to draw liquid upwardly in the column from the reservoir. This may be achieved by increasing the air pressure for a given jet size or by increasing the size of the jets for a given air pressure. It is not essential for all of the air jets or all of the outlet apertures in the apparatus to be of uniform size. Combinations of different sized pairs of apertures may be provided and the aligned pairs of air jets and outlet aperture may be at different angles around the nebulizer head so that the aerosol dispersion is distributed throughout an increased volume of space within the apparatus. The relative dimensions of the duct 13, jets 16, and outlet apertures 20, may together be scaled up or down to suit the particular requirements of the device.

It has been found that restricting the flow of the aerosol through the outlet apertures 20 increases the forces drawing liquid from the reservoir so that the apparatus is, in effect, self-cleaning, preventing a deposition of liquid/solids around the apertures. Also, operation of the apparatus may be controlled by shuttering the outlets as required from a fully closed to fully open condition. Operation will not be unduly impaired by one or more of the jets or apertures becoming blocked or shuttered, whilst others remain open.

The device may be modified by rotating one or more parts of the nebulizer assembly so that, for example, in FIG. 3 the baffle 21 could be rotated or alternatively the air jet assembly may be rotated relative to or in synchronism with a part of the duct 13 containing the outlet apertures 20. Spinning of part or all of the apparatus in this way may be utilized to increase the draw of liquid from the reservoir or the extent of secondary aerosolization, or in separation applications when a fraction of particles within the aerosol may be separated by centrifugal forces.

The principal advantage achieved by a nebulizer made in accordance with the invention is that materials containing or even in the form of solids may be dispersed without blockage of the apparatus, whilst at high gas pressures, the particles may emerge from the orifices without excessive physical damage whereby the device may be applied to the dispersion of delicate materials.

It is not intended to limit the invention to the above examples only, many variations such as might readily occur to one skilled in the art, being possible without departing from the scope of the invention as defined by the appended claims.

For example, whilst the wall 13 of the duct is preferably circular in cross-section, other shapes may be suitable with commensurate similar configuration of the body 15 containing the air jets 16.

An additional advantage may be attained by applying reduced pressure at the outlet 12 thus positively to draw larger volumes of the product dispersion from the device. A similar effect would result from providing an in-line fan within the vessel 10 forcing the dispersion through the outlet. In this way, humidification of large gas volumes, or rapid evaporation of liquids may be achieved.

In the embodiment illustrated in FIG. 1, a typical figure for droplet concentration obtained using a six-jet device with a jet diameter of 1.1 mm and an outlet aperture diameter of 4 mm, operating at 15 p.s.i., is $2.2 \times 10^3$ cm$^{-3}$ with a mean droplet diameter of 3.53 $\mu$m.

In the embodiment illustrated in FIG. 3, with the addition of a baffle, the droplet concentration increases to, for example, $8.0 \times 10^3$ cm$^{-3}$ with a mean diameter of 3.78 $\mu$m.

Appropriate selection of air jet and outlet diameters, allows the device to operate at air pressures as low as 2.5 p.s.i., for example, with air jet at 1.5 mm and outlet at 3 mm.

We claim:

1. A device for producing a particulate dispersion comprising at least one duct to contain a supply of a fluid material to be dispersed, a plurality of outlet apertures communicating with said at least one duct and directed normal to the longitudinal axis of said at least one duct, and a plurality of pressurized gas jets aligned with the outlet apertures to draw material from said at least one duct and to form a dispersion of the material which is thus forced through the apertures, characterized in that the cross-sectional area of each outlet aperture is not greater than the cross-sectional area of the at least one duct communicating therewith, and wherein at least a part of the at least one duct is located upright in a vessel for containing a reservoir of the fluid material to be dispersed, an open bottom end of the at least one duct being located such that it will be submerged within the material in use.

2. A device according to claim 1, in which the combined cross-sectional area of the outlet apertures is less than that of the at least one duct.

3. A device according to claim 1, wherein the outlet apertures and gas jets are located at the top of the at least one duct and within the walls of the vessel such that large droplets within the dispersion may impinge upon the vessel walls and return to the reservoir, the top of the vessel including an opening through which a substantial part of the dispersion may issue, means being provided to induce a positive flow of the dispersion through the opening.

4. A device according to claim 1, wherein there is a single duct and the pressurised gas jets are fed from a line which passes longitudinally through the interior of the duct.

5. A device according to claim 1, wherein there is a single duct and the gas jets are defined within a body fixed within the top of the duct.

6. A device according to claim 1, wherein there is a single duct and the gas jets are fed from a line which enters the top of the duct from outside the latter leaving the entire duct free to transport a single column of said material from the reservoir.

7. A device according to claim 1, including a baffle which surrounds the at least one duct in the region of the outlet apertures and presents, adjacent each aperture an outwardly diverging surface upon which larger droplets within the dispersion may impinge.

8. A device according to claim 7, in which said outwardly diverging surface is curvilinear.

9. A device according to claim 1, wherein the diameter of each gas jet is between 0.7 and 1.3 mm, wherein the diameter of each outlet aperture is between 3 mm and 6 mm, and wherein the cross-sectional area of the at least one duct is between 140 sq. mm and 420 sq. mm.

* * * * *